(12) United States Patent
Windolf

(10) Patent No.: US 8,585,742 B2
(45) Date of Patent: Nov. 19, 2013

(54) BONE FIXATION DEVICE

(75) Inventor: Markus Windolf, Davos (CH)

(73) Assignee: AO Technology AG, Chur (CH)

( * ) Notice: Subject to any disclaimer, the term of this patent is extended or adjusted under 35 U.S.C. 154(b) by 360 days.

(21) Appl. No.: 13/058,715

(22) PCT Filed: Aug. 15, 2008

(86) PCT No.: PCT/CH2008/000349
§ 371 (c)(1),
(2), (4) Date: Feb. 11, 2011

(87) PCT Pub. No.: WO2010/017649
PCT Pub. Date: Feb. 18, 2010

(65) Prior Publication Data
US 2011/0144646 A1 Jun. 16, 2011

(51) Int. Cl.
*A61B 17/80* (2006.01)
(52) U.S. Cl.
USPC ............. 606/282; 606/257; 606/71; 606/281; 606/105
(58) Field of Classification Search
USPC ......... 606/254–259, 280–283, 298, 299, 105, 606/86 B, 902–906, 915; 623/17.13, 17.15
See application file for complete search history.

(56) References Cited

U.S. PATENT DOCUMENTS

| | | | |
|---|---|---|---|
| 4,289,123 A | | 9/1981 | Dunn |
| 5,375,823 A | | 12/1994 | Navas |
| 6,036,693 A | * | 3/2000 | Yuan et al. ................. 606/250 |
| 7,008,427 B2 | * | 3/2006 | Sevrain .......................... 606/71 |
| 8,109,975 B2 | * | 2/2012 | Veldman et al. ............. 606/257 |
| 2003/0204190 A1 | | 10/2003 | Li |
| 2005/0075633 A1 | * | 4/2005 | Ross ............................... 606/61 |
| 2008/0015589 A1 | | 1/2008 | Hack |
| 2008/0183213 A1 | | 7/2008 | Veldman et al. |

FOREIGN PATENT DOCUMENTS

WO 2006/111852 10/2006
WO 2007050276 5/2007

OTHER PUBLICATIONS

International Preliminary Report on PatentabilityWritten Opinion of International Patent Application No. PCTCH2008/000349; Feb. 24, 2011.

* cited by examiner

*Primary Examiner* — Michael T Schaper
(74) *Attorney, Agent, or Firm* — Rankin, Hill & Clark LLP

(57) ABSTRACT

A bone fixation device (1) for internal fixation of bone fragments with a longitudinal axis (2) and comprising: A) a first and a second plate (3, 4) each having a lower surface (5), an upper surface (6), two lateral surfaces (22, 23), a front surface (7) axially intermediate between said first and second plate (3, 4), an axially terminal surface (8) and at least one screw hole (17) extending from said upper surface (6) to said lower surface (5) and intended to receive a bone screw; B) a first and a second guide rail (13, 14) arranged parallel with respect to said longitudinal axis (2) and uniaxially slideably connecting said first and second plate (3, 4); and C) at least one resilient member (15, 16) arranged between said first and second plate (3, 4) acting as a compression spring.

17 Claims, 1 Drawing Sheet

BONE FIXATION DEVICE

FIELD OF THE INVENTION

Figures 1, 2:
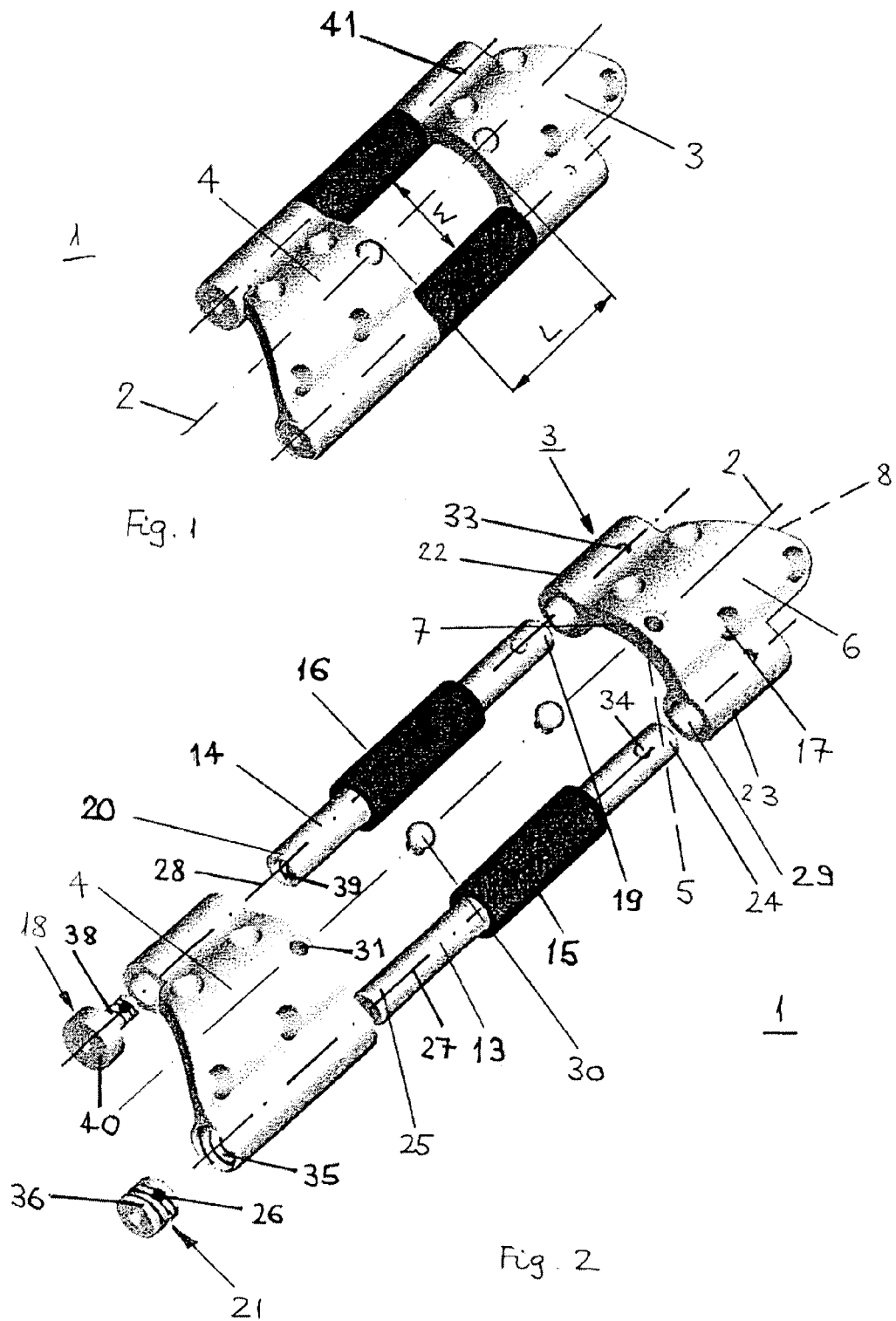

The invention relates to a bone fixation device according to the preamble of claim 1, a method for preparation of a pre-assembled bone fixation device prior to implantation according to the preamble of claim 14 and to a method for bone fixation according to the preamble of claim 15.

Long bone fractures lacking bone support after fixation, e.g. comminuted zones or critical size defects at highly loaded sites set high demands on the fixation device. The known external fixation devices have the disadvantage of long lever arms such rendering more difficult a rigid stabilization of the bone fragments with elimination of bending and shear.

Further, bone healing is known to be accelerated by mechanical stimulation of the defect site. External bone fixation devices allowing an interfragmentary movement of a fracture, the so-called dynamisation of the fracture are frequently applied. This technique allows to control the loading of the fracture during the healing process, i.e. to enhance bone formation. However, such external fixators are bulky and can be hindering in the daily life of the patient. Moreover, the infection risk can be significantly reduced with internal fixation.

DESCRIPTION OF THE PRIOR ART

An orthopedic bone plate including an elongated member with two or more fixation parts which can be uniaxially displaced relative to each other and an elastic cable which is longitudinally stretched and coupled in tension to the fixation parts is known from USA 2008/0015589 HACK. The elastic cable causes the fixation parts to contract in the longitudinal direction such contracting the bone fragments. This known bone plate is configured to stabilize and splint the fracture during healing. The bone plate is not provided with means to allow a coaxial compressive load transmission upon physiologically loading the bone.

An intervertebral stabilization device comprising a cylindrical telescopable member connecting two adjacent vertebral bodies and damping means acting as springs with respect to a longitudinal compression or distraction of the telescopable member is known from U.S. Pat. No. 5,375,823 NAVAS. This known device is not configured to prevent a relative rotation of the two parts forming said cylindrical telescopable member and would therefore not be suitable to stabilize a long bone fracture particularly with respect to shear stresses.

A further spinal fixation device allowing to adjust a spacing between two brackets attached to adjacent vertebral bodies is known from U.S. Pat. No. 4,289,123 DUNN. This known device comprises a rigid connection between the two brackets and would therefore not allow a defined axial motion of the two vertebral bodies towards each other when a physiological load is applied.

SUMMARY OF THE INVENTION

It is an object of the invention to provide a bone fixation device allowing a defined uniaxial motion of the bone fragments upon physiologically loading the bone as well as a predeterminable load apportion between the bone and the implant.

The invention solves the posed problem with a bone fixation device that displays the features of claim 1, a method for preparation of a pre-assembled bone fixation device prior to implantation that displays the features of claim 14 and with a method for bone fixation that displays the features of claim 15.

The bone fixation device according to the invention offers the advantages that:
- due to the two parallel guide rails the two plates cannot rotate relative to each other about any axis, in particular the longitudinal axis such allowing a high stability of the fracture fixation particularly with respect to shear stresses;
- accelerated bone healing by mechanical stimulation of the fracture site due to the non-rigid dynamic fixation of the bone fragments relative to one another; and
- the compressible resilient member enables a predeterminable load sharing situation between the bone and the implant when physiologically loaded.

The screw holes in said first and second plate are preferably provided with locking means allowing a rigid angularly stable anchoring of the screw heads in the screw holes.

By means of the method for implantation of a bone fixation device according to the invention a dynamisation of the fracture can be effected after a certain bone consolidation.

In a special embodiment said bone fixation device comprises a first and a second resilient member arranged between said first and second plate.

In a further embodiment said first and second resilient member each envelopes one of said first and second guide rails.

In another embodiment said first and second plate are arranged in a common plane.

In yet another embodiment said plane is curved, preferably forming a segment of a circular cylindrical surface. This configuration of the bone fixation device allows the advantage that the plates do not show a large span such that the device can be used for relatively thin long bones. Further, an increased stability of the bone fixation device can be achieved and the bone screws can be set in a desired variable angle. Preferably, the radius of curvature is greater than 12 mm, typical in an application for a sheep tibia would be a radius of curvature of 15 mm.

In still a further embodiment said first and second plate form a segment of a hollow circular cylinder extending over an arc of minimum 60°, preferably minimum 90°. This allows the advantages that an increased stability of the bone fixation device can be achieved and the bone screws can be set in a desired variable angle, e.g. 45-80°, a typical angle between two screw hole axes is 60°.

In another embodiment said first and second plate form a segment of a hollow circular cylinder extending over an arc of maximum 180°.

In a further embodiment said first and second guide rail each has a first and a second end wherein said first ends are axially fixed to said first plate and said second ends are axially displaceably connected to said second plate and wherein a set member is arranged in said second plate by means of which the maximum axial displacement of said second plate towards said first plate can be adjusted. Such configuration of the bone fixation device allows the advantage that the axial shortening of the bone fixation device can be adjusted. By means of said set member, e.g. a set screw screwed into the bore in said second plate which serves as a guidance for one of the guide rails an axial compression of the bone fixation device up to maximum 3-4 mm can be adjusted.

In another embodiment a tension member is axially and threadedly connected to said second end of said second guide rail and axially kept at said second plate against movements towards said front surface of said second plate such that by means of said tension member said first and second resilient member can be axially compressed and pre-stressed. The pre-stressing of the resilient member allows to apportion the load between the implant and the bone which is applied upon physiological loading of the bone. Typical dimensions would be in case of a bone fixation device for a sheep tibia pre-compression of said resilient members about 1 mm;
pre-load about 100 N; and
spring rate of the resilient members about 50 N/mm.

In yet a further embodiment said set member and said tension member are configured as set screws each provided with an insert which is located in a transverse cavity in said set screw. By means of said inserts, preferably nylon inserts an undesired rotation, e.g. loosening of the set screws can be prevented. The set screws are preferably provided with a thread having a 0.5 mm slope.

In another embodiment said front surfaces of said first and second plate and said first and second guide rails enclose a free opening with a width W>0 measured orthogonal to said longitudinal axis and a length L>0 measured parallel to said longitudinal axis. This free opening allows the advantage of an optimal visibility of the fracture site during radiographic imaging for follow-up monitoring of the healing. Typical dimensions would be for said width about 20 mm and for said length about 35 mm.

In yet another embodiment said first and second resilient members are configured as tubular sleeves arranged coaxially on said first and second guide rail. Typical dimensions in case of a bone fixation device for a sheep tibia are:

length of the resilient members about 37 mm;
external diameter of the resilient members about 12 mm;
internal diameter of the resilient members about 8 mm;
Shore hardness 90; and
spring rate about 50 N/mm.

In again a further embodiment each said first and second plates is provided with a reference element including a convex, preferably hemi-spherical portion protruding out over said upper surface of said first and second plate. The advantage of this configuration is that the protruding spherical portions allow to measure the displacement of the implant in-vivo. The protruding spherical portions are detectable under the skin. Such by means of an e.g. mechanical displacement transducer equipped with conical recesses to be seated above the spherical portions on the skin the displacement of the first and second plate relative to each other can be measured.

In another embodiment said first and second resilient member are made of a biocompatible material, preferably a bioresorbable material. A material with biodegradable characteristics allows the advantage of reducing the portion of the load transferred via the implant with ongoing bone consolidation. Typical materials for resilient members are bioresorbable polyurethane (PUR) or polylactide (PLA).

A BRIEF DESCRIPTION OF THE DRAWINGS

One preferred embodiment of the invention will be described in the following by way of example and with reference to the accompanying drawings in which:

FIG. 1 illustrates a perspective view of an embodiment of the device according to the invention in the assembled state; and FIG. 2 illustrates an exploded view of the embodiment of FIG. 1.

FIGS. 1 and 2 illustrate an embodiment of the bone fixation device 1 according to the invention comprising a longitudinal axis 2, a first and a second plate 3, 4 each having a lower surface 5, an upper surface 6, two lateral surfaces 22, 23, a front surface 7 located axially intermediate between said first and second plate 3, 4, an axially terminal surface 8 and four screw holes 17 each extending from said upper surface 6 to said lower surface 5 and intended to receive a bone screw. Said screw holes 17 are provided with a rigid fixation means (not shown), e.g. conical internal threads for an angular stable anchoring of the corresponding heads of the bone screws.

Further, a first and a second guide rail 13, 14 is arranged parallel with respect to said longitudinal axis 2 such uniaxially slideably connecting said first and second plate 3, 4. A first and a second resilient member 15, 16 is arranged between said first and second plate 3, 4. Said first and second resilient members 15, 16 are configured as tubular sleeves each enveloping one of said first and second guide rails 13, 14 whereby said first and second resilient members 15, 16 are arranged coaxially to the first and second central axes 27, 28 of said first and second guide rail 13, 14.

Said first and second plate 3, 4 are arranged in a common plane which is curved in the form a segment of approximately one third of a circular cylindrical surface the axis of which is parallel to said longitudinal axis 2 of said bone fixation device 1. Each of said plates 3, 4 comprises a curved central plate and two hollow cylindrical members with a central bore 29 each for partially receiving said first and second guide rail 13, 14 which have a circular cylindrical shape in the present embodiment. Said central bores 29 in said first plate 3 can be through bores or pocket holes.

Said first and second guide rail 13, 14 each has a first and a second end 19, 20, 24, 25. Said first ends 19, 24 are axially fixed to said first plate 3 by means of transverse alignment pins 41 which are each pressed into corresponding bore holes 33, 34 located in said first plate 3 and said first and second guide rail 13, 14. Said bore holes 33, 34 are arranged orthogonally to said first and second central axes 27, 28 of said first and second guide rail 13, 14.

Said second ends 20, 25 are slideably inserted in said central bores 29 of said second plate 4 such that said first and second guide rail 13, 14 is axially displaceably connected to said second plate 4. The central bores 29 of said second plate 4 are configured as through holes. Further, a set member 21 in the form of a first set screw 36 is arranged in said second plate 4 by means of which the maximum axial displacement of said second plate 4 towards said first plate 3 can be adjusted. For this means said first set screw 36 can be advanced in an interior thread 35 arranged within that one of said central bores 29 in said second plate 4 which receives said first guide rail 13. By means of said set member 21, i.e. said first set screw 36 the maximum axial compression of the bone fixation device can be adjusted.

In order to pre-compress said first and second resilient member 15, 16 a tension member 18 in the form of a second set screw 38 can be advanced in a second interior thread 39 penetrating from said second end 20 of said second guide rail 14 into said second guide rail 14. Said second set screw 38 comprises a screw head 40 abutting said terminal surface 8 of said second plate 4 such being axially kept at said second plate 4 against movements towards said front surface 7 of said second plate 4. By means of said second set screw 38 which acts as tension member 18 said first and second resilient member 15, 16 can be axially compressed and pre-stressed such allowing to pre-load said first and second resilient member 15, 16 which results in a higher spring force of said first and second resilient member 15, 16 when an initial physiological load is applied to said bone fixation device 1.

Each of said first and second set screws 36, 38 is provided with a nylon insert 26 which is pressed in a transverse cavity in said first and second set screw 36, 38. The insert 26 protrudes out into the threads of said first and second set screw 36, 38 such preventing said first and second set screw 36, 38 from an undesired rotation such as loosening. By means of a free opening enclosed by said front surfaces 7 of said first and second plate 3, 4 and said first and second guide rails 13, 14 with a width W=20 mm measured orthogonal to said longitudinal axis 2 and a length L=36 mm measured parallel to said longitudinal axis 2 an optimal visibility of the fractures site is achieved.

Each of the first and second plate 3, 4 comprises a through hole 31 arranged close to the front surface 7 of said first and second plate 3, 4 and penetrating through said first and second plate 3, 4 from the upper surface 6 and the hole axes of which cut said longitudinal axis 2 of said bone fixation device 1. A reference element 30 including a hemi-spherical head is screwed into said pocket holes 31 each 13. Said reference elements 30 include a convex, preferably hemi-spherical portion protruding out over said upper surface 6 of said first and second plate 3, 4. The protruding spherical portions are detectable under the skin. Such by means of an e.g. mechanical displacement transducer equipped with conical recesses to be seated above the spherical portions on the skin the displacement can be measured.

Brief Description of the Preparation and the Surgical Procedure:

The preparation of a pre-assembled bone fixation device prior to implantation essentially comprises the steps of:
  sterilizing the complete parts of the bone fixation device 1 in the pre-assembled state including mounted first and second guide rails 13, 14 and reference elements 30;
  fitting the first and second resilient member 15, 16 on one of the first and second guide rails 13, 14 each;
  attaching said second plate 4 to said first and second guide rail 13, 14;
  tightening said tension member 18, i.e. said second set screw 38 until said first and second resilient member 15, 16 are compressed to a certain preload. The distance between the front surfaces 7 of said first and second plate 4 can be measured interoperatively with a calliper;
  tightening said set member 21, i.e. said first set screw 36 until contact to said first guide rail 13 is achieved such that said first and second plate 3, 4 are axially locked and cannot be axially displaced towards each other; and
  turning back said set member 21, i.e. said first set screw 36 for a desired possible axial displacement of said second plate 4 towards said first plate 3 upon being physiologically loaded. This step is optional since before a certain bone consolidation has started a dynamisation of the fracture might not be advisable. Then this step would be effected after a certain time period subsequent to implantation of the bone fixation device as described below.

An implantation of the bone fixation device essentially comprises the further steps of:
  placing said bone fixation device 1 over a fracture site in its pre-compressed and locked state;
  predrilling holes in the bone for bone fixation screws aligned with said screw holes 17 in said first and second plate 3, 4 using a standard drill sleeve;
  advancing bone screws into said screw holes 17 and said predrilled holes in the bone and tightening them;
  closing the incision;
  establishing another small incision after a desired time period for a suitable bone consolidation allowing insertion of an instrument to manipulate said set member 21; and
  turning back said set member 21 for a desirable possible axial displacement of said second plate 4 towards said first plate 3.

While various descriptions of the present invention are described above, it should be understood that the various features can be used singly or in any combination thereof. The scope of the present invention is accordingly defined as set forth in the appended claims.

What is claimed is:

1. A bone fixation device for internal fixation of bone fragments, the bone fixation device having a longitudinal axis and comprising:
  a first plate and a second plate each having a lower surface, an upper surface, two lateral surfaces, a front surface axially intermediate between said first plate and second plate, an axially terminal surface, and at least two screw holes extending from said upper surface to said lower surface for receiving bone screws;
  a first guide rail and a second guide rail arranged parallel with respect to said longitudinal axis and uniaxially slideably connecting said first plate and said second plate; and
  at least one resilient member arranged between said first plate and said second plate, said at least one resilient member acting as a compression spring;
  wherein said first guide rail and said second guide rail each have a first end and a second end, the second end of the second guide rail having an interior thread penetrating therein,
  wherein a tension member is axially and threadedly connected to said second end of said second guide rail and axially kept at said second plate against movement toward said front surface of said second plate, and
  wherein the tension member is in the form of a set screw, which can be advanced in said interior thread penetrating into said second end of said second guide rail.

2. The bone fixation device according to claim 1, wherein said at least one resilient member comprises a first resilient member and a second resilient member arranged between said first plate and said second plate.

3. The bone fixation device according to claim 2, wherein said first resilient member and said second resilient member each envelops one of said first guide rail and said second guide rail.

4. The bone fixation device according to claim 2, wherein said first resilient member and said second resilient member are configured as tubular sleeves arranged coaxially on said first guide rail and said second guide rail.

5. A method for preparing a bone fixation device according to claim 2 which has been pre-assembled, for implantation, the method comprising the steps of:
  tightening said tension member until said first resilient member and said second resilient member are compressed to a desired preload;
  tightening a set member arranged in said second plate until said first plate and said second plate are axially locked and cannot be axially displaced towards each other; and
  turning back said set member to allow for a desired possible axial displacement of said second plate towards said first plate upon being physiologically loaded.

6. The bone fixation device according to claim 1, wherein said first plate and said second plate are arranged in a common piece of reference geometry.

7. The bone fixation device according to claim 6, wherein said common piece of reference geometry is curved.

8. The bone fixation device according to claim 7, wherein said first plate and said second plate form a segment of a hollow circular cylinder extending over an arc of minimum 60°.

9. The bone fixation device according to claim 7, wherein said first plate and said second plate form a segment of a hollow circular cylinder extending over an arc of maximum 180°.

10. The bone fixation device according to claim 7, wherein said common piece of curved reference geometry defines a segment of a hollow circular cylindrical surface.

11. The bone fixation device according to claim 7, wherein said first plate and said second plate form a segment of a hollow circular cylinder extending over an arc of minimum 90°.

12. The bone fixation device according to claim 1, wherein said first ends of said first guide rail and said second guide rail are axially fixed to said first plate, and wherein said second ends of said first guide rail and said second guide rail are axially displaceably connected to said second plate, and wherein a set member is arranged in said second plate by and can be advanced in an interior thread arranged in a central bore in the second plate.

13. The bone fixation device according to claim 12, wherein said set member is configured as a set screw, the set screws defining the tension member and the set member each being provided with an insert which is located in a transverse cavity in each set screw.

14. The bone fixation device according to claim 1, wherein said front surfaces of said first plate and said second plate and said first guide rail and said second guide rail enclose a free opening with a width W>0 measured orthogonal to said longitudinal axis and a length L>0 measured parallel to said longitudinal axis.

15. The bone fixation device according to claim 1, wherein each of said first and second plates is provided with a reference element including a convex portion protruding out over said upper surface of said first and second plate.

16. The bone fixation device according to claim 15, wherein the convex portion is hemi-spherical in shape.

17. A method for fixating a bone at a fracture site comprising the steps of:
  placing a bone fixation device according to claim 1 in a pre-compressed and locked state over the fracture site via an incision;
  predrilling holes in the bone for receiving said bone screws aligned with said at least two screw holes in said first plate and said second plate;
  advancing said bone screws into said at least two screw holes and said predrilled holes in the bone and tightening them;
  closing the incision;
  establishing another small incision after a desired time period for a suitable bone consolidation, said another small incision allowing for insertion of an instrument to manipulate a set member arranged in said second plate; and
  turning back said set member using the instrument for a desirable possible axial displacement of said second plate towards said first plate.

* * * * *